US007527810B1

(12) United States Patent
Thanavala et al.

(10) Patent No.: US 7,527,810 B1
(45) Date of Patent: May 5, 2009

(54) ORAL IMMUNOLOGY USING PLANT PRODUCT CONTAINING HEPATITIS SURFACE ANTIGEN

(75) Inventors: Yasmin Thanavala, Williamsville, NY (US); Charles Joel Arntzen, Ithaca, NY (US); Hugh S. Mason, Ithaca, NY (US)

(73) Assignees: Health Research, Inc., Buffalo, NY (US); Boyce Thompson Institute for Plant Research, Inc, Ithaca, NY (US)

( * ) Notice: Subject to any disclaimer, the term of this patent is extended or adjusted under 35 U.S.C. 154(b) by 0 days.

(21) Appl. No.: 09/420,695

(22) Filed: Oct. 19, 1999

Related U.S. Application Data

(63) Continuation-in-part of application No. 09/418,177, filed on Oct. 13, 1999, now abandoned.

(51) Int. Cl.
*A01N 65/00* (2006.01)
*A01N 63/02* (2006.01)
*A61K 45/00* (2006.01)
*A61K 39/00* (2006.01)
*A61K 39/29* (2006.01)

(52) U.S. Cl. .................... 424/725; 424/282.1; 424/780; 424/132.1; 424/227.1; 514/894

(58) Field of Classification Search .................... None
See application file for complete search history.

(56) References Cited

U.S. PATENT DOCUMENTS

| | | | |
|---|---|---|---|
| 5,182,109 A | | 1/1993 | Tamura et al. |
| 5,484,719 A | | 1/1996 | Lam et al. |
| 5,612,487 A | | 3/1997 | Lam et al. |
| 5,654,184 A | | 8/1997 | Curtiss, III et al. |
| 5,679,880 A | | 10/1997 | Curtiss, III et al. |
| 5,686,079 A | | 11/1997 | Curtiss, III et al. |
| 5,914,123 A | * | 6/1999 | Arntzen et al. |
| 5,935,570 A | * | 8/1999 | Koprowski et al. |

FOREIGN PATENT DOCUMENTS

WO WO 94/20135 9/1994
WO WO 00/37610 6/2000

OTHER PUBLICATIONS

Stites et al. Basic and Clinical Immunology, 7th ed., Appleton & Lange. Chapter 58: Immunization by Grossman et al. pp. 723-741, 1991.*
Stites et al. Basic and Clinical Immunology, 7th ed., Appleton & Lange. Chapter 58: Immunization by Grossman et al. pp. 102, 723-741, 1991.*
H. Mason, et al., "Expression of hepatitis B surface antigen in transgenic plants", Proc. Natl. Acad. Sci. USA, vol. 89, pp. 11745-11749, Dec. 1992.
Y. Thanavala, et al., "Immunogenicity of transgenic plant-derived hepatis B surface antigen", Proc. Natl. Acad. Sci. USA, vol. 92, pp. 3358-3361, Apr. 1995.
"The Women in the Lab Coats . . . Breaking New Ground", Roswellness, vol. 2, No. 1, pp. 12-13, 1999.
Aizpurua, H.J., et al., "Oral Vaccination: Indentification of Classes of Proteins that Provoke an Immune Response upon Oral Feeding", J. Exp. Med., 1988, pp. 440-451, vol. 167.
Ehsani, P., et al., "Polypeptides of Hepatitis B Surface Antigen Produced in Transgenic Potato", Gene, 1997, pp. 107-111, vol. 190.
Kapusta, J., et al., "A Plant-Derived Edible Vaccine Against Hepatitis B Virus", Faseb J., 1999, pp. 1796-1799, vol. 13, No. 13.

* cited by examiner

*Primary Examiner*—Michele Flood
(74) *Attorney, Agent, or Firm*—Michael L. Dunn

(57) ABSTRACT

A method for obtaining an immune response to hepatitis B surface antigen (HBsAg) by feeding the antigen in a plant material to an animal that is immunoreceptive to the HBsAg. It has now been discovered that the animal may be made immunoreceptive to HBsAg either by administering the plant material containing HBsAg in conjunction with a suitable adjuvant or by prior primary immunization. When the animal is made immunoreceptive by a prior, e.g. primary, immunization, an immune response to HBsAg may be boosted in the animal by feeding the animal the plant material containing the HBsAg. For example, an animal, e.g. a human, that previously had a positive response to primary immunization against hepatitis B, can have a booster response to HBsAg by feeding the animal the antigen in a plant material. The plant material is a substance comprising a physiologically acceptable plant material, especially potatoes, containing hepatitis B surface antigen (HBsAg). The HBsAg in the plant results from expression by the plant of HBsAg due to genetic alteration.

16 Claims, No Drawings

ORAL IMMUNOLOGY USING PLANT PRODUCT CONTAINING HEPATITIS SURFACE ANTIGEN

This is a Continuation-in-Part of U.S. patent application Ser. No. 09/418,177, filed Oct. 13, 1999 now abandoned for ORAL IMMUNOLOGY USING PLANT PRODUCT CONTAINING HEPATITIS SURFACE ANTIGEN by Yasmin Thanavala and Charles Joel Arntzen.

STATEMENT REGARDING FEDERALLY SPONSORED RESEARCH

This invention was made with funding from the National Institute of Health award AI 42836, AI 27976. The United States Government may have certain rights in this invention.

BACKGROUND OF THE INVENTION

Hepatitis B virus (HBV) is responsible for significant morbidity and mortality in spite of the availability of efficacious parenteral vaccines. In 1996 it was estimated that some 115 million people were infected with HBV. Mortality caused by this disease is estimated to be 1 million cases per year. In developed countries such as the US, immunization rates for HBV remain below targeted objectives and there are over 300,000 new cases annually and 5,000 deaths each year as a result of HBV infection. In addition, a review of the prevalence of HBV infection in the US between 1976 and 1994 indicated that there was no significant decrease in HBV infection during that period, despite the availability of hepatitis B vaccine. Thus, in developed countries there is a need to improve the availability of and access to effective alternatives to the current parenteral vaccines. This is even more important as the number of vaccines that are becoming part of childhood immunizations increases since there are practical considerations in how to safely and effectively administer the multiple antigens that are becoming part of the pediatric immunization schedule.

Another concern is that a significant proportion of the global morbidity and mortality is localized in developing countries where HBV is endemic. As an example, in rural Malawi evidence of HBV infection was found in 72% of women delivering in hospital and chronic carriage was 13%. In these settings, current parenteral vaccines are of limited availability because of the need for cold storage and the significant cost of the vaccines. While significant initiatives have begun to address the issue of how to provide hepatitis B vaccines to developing countries, alternative approaches are needed. Although immunization rates in developed countries may be on the increase, in the absence of an effective global immunization program for hepatitis B, there will continue to be importation of hepatitis B disease into developed countries from developing countries.

An alternative to parenteral immunizations for a few diseases are vaccines that can be delivered orally. A specific approach to oral immunization has been proposed by expressing antigens in transgenic plant tissue followed by ingestion. This technique, in one step might have the potential to provide both a less complex manufacturing process and to provide the antigen in a "matrix" that would be suitable for oral immunization. In addition, plant tissues, such as potato tubers, have a distinct advantage in that vegetables, even in the raw state, have a long history of safety in the marketplace. Lastly, transgenic plant tissue expressing antigens that are delivered orally may have the added advantage that both humoral and mucosal immunity could be stimulated, resulting in the potential to protect mucosal surfaces more effectively than parenteral immunization alone might accomplish. Plants expressing hepatitis B surface antigen (HBsAg) have in fact been developed but have also disappointingly been found not to create a protective immune response in animals ingesting them even though HBsAg isolated from such plants have been found to raise an immune response when administered parenterally.

BRIEF DESCRIPTION OF THE INVENTION

Transgenic plants, e.g. potatoes, have been developed that express hepatitis B surface antigen, an antigen known to raise an immune response to hepatitis B when parenterally administered. Unfortunately it has been found that such an immune response is not raised when the plant, e.g. potato, is simply fed to an animal.

It has, however, now been unexpectedly discovered that an immune response to hepatitis B surface antigen (HBsAg) may be obtained when the antigen in a plant material is fed to the animal when the animal is immunoreceptive to the HBsAg. It has now been discovered that the animal may be made immunoreceptive to HBsAg either by administering the plant material containing HBsAg in conjunction with a suitable adjuvant. The animal may also be immunoreceptive due to a prior, e.g. primary, immunization in which case an immune response to HBsAg may be boosted in the animal by feeding the animal the plant material containing the HBsAg. For example, an animal, e.g. a human, that previously had a positive response to primary immunization against hepatitis B, can have a booster response to HBsAg by feeding the animal the antigen in a plant material. The plant material is a substance comprising a physiologically acceptable plant material, especially potatoes, containing hepatitis B surface antigen (HBsAg). The HBsAg in the plant results from expression by the plant of HBsAg due to genetic alteration.

DETAILED DESCRIPTION OF THE INVENTION

The plant from which the desired plant material is obtained may be essentially any plant provided that the plant material contains HBsAg. Plants may be made to express HBsAg by transgenic alteration. Almost any plant suitable for ingestion can be altered to express HBsAg, but the most preferred plants are food plants, e.g. plants that produce fruits, grains, and vegetables, such as bananas, potatoes and tomatoes. Especially preferred are plant materials that do not contain significant quantities of acid, e.g. tubers such as potatoes, since the acid in certain plant materials, such as tomatoes or citrus fruits, may cause degradation of the HBsAg. Further, plant materials that contain significant quantities of protease enzymes, e.g. papayas, may not be desirable since such enzymes could also degrade the HBsAg. A "significant" quantity as used herein, means a quantity that will cause antigen degradation.

Methods for genetic alteration of tobacco plants to express HBsAg are already known to those skilled in the art, e.g. as described in Mason, et al. "Expression of hepatitis B surface antigen in transgenic plants", Proc. Natl. Acad. Sci. USA, Vol. 89, pp. 11749, December 1992. This article is incorporated by reference as background art. Tobacco is unfortunately not suitable for ingestion and is thus not physiologically acceptable. In accordance with the invention, it has been discovered that similar methods may be used to genetically alter other plants to express HBsAg. Especially suitable plants, are plants of the family solanaceae, especially potatoes. Details for altering potatoes are given infra.

The plant used in accordance with the invention should contain at least 5 µg and preferably from about 7 µg to about 15 µg of HBsAg per gram of plant material to be ingested. The animal, e.g. a human, should ingest sufficient plant material to provide from about 10 to about 100 micrograms of hepatitis B surface antigen per kilogram of body weight. The animal, e.g. a human, will usually ingest sufficient plant material to provide from about 2 to about 5 grams of plant material per kilogram of body weight.

Immune response is increased if a series of ingestions of the plant material is undertaken, e.g. a series of three, each ingestion being separated by at least five and preferably by at least about seven to fourteen days.

The plant material of the invention does not raise a significant immune response when administered orally in the absence of the required method steps of the invention. In accordance with the invention, the plant material containing HBsAg must be orally administered either to a subject that has previously had a primary immunization, e.g. by parental injection or must be orally administered in conjunction with a suitable adjuvant that effectively causes the HBsAg to raise a response. Prior to the present invention it was not predictable that an immune response to HBsAg could be raised to a plant material containing HBsAg when the plant material was ingested either by a subject having had a previous primary immunization or in conjunction with an adjuvant.

Adjuvants that may be effective include bacterial plasmid DNA, anti-HB antibody, oligodeoxynucleotides containing immunostimulatory CpG, modified cholera toxin (CT), modified *E. coli* heat stable lymphotoxin, lypophilic derivative of muramyl dipeptide (MDP-Lys (L18)), aluminum phosphate or aluminum sulfate, cytokines, core protein of hepatitis C. A significant number of human subjects having previously received a primary immunization show an immune booster response when treated in accordance with the method of the present invention, e.g. sixty percent or more of subjects. It must, however, be understood that a number of subjects may not obtain a measurable booster response, often for reasons not well understood. Among such reasons may be that the subject, even though previously receiving a primary immunizing treatment, may not in fact have had a strong primary immune response or there has been sufficient time lapse since the primary immunization that there are too few memory cells remaining in the subject. Similar results may occur with known vaccines, no matter how they are administered, i.e. there may be subjects that do not respond.

The invention may be illustrated by the following examples.

Animals were fed potatoes that expressed and contained HBsAg and anti-hepatitis B response was measured by enzyme immunoassay.

The potato was chosen as a preferred example of a plant that can be used in accordance with the invention for a number of reasons. In particular, the potato is relatively acid neutral when compared with other plant materials, especially certain fruits. Further, there have been a number of studies conducted on the potato with respect to its genetic character and possible transgenic modification. Most importantly, potatoes are a staple food and usual individual consumption is estimated at 1 to 100 kg per person per year worldwide. U.S. average individual consumption has been estimated at 36 kg per annum. In addition, potato is eaten in the U.S. as a raw vegetable and is cited in the Code of Federal Regulations [21 CFR 101.44(b)] among the 20 most frequently eaten raw vegetables. The specific cultivar of potato used to create the current HBV-EPV transgenic plants, in accordance with these specific examples, has also been used to create transgenic plants expressing other antigens. Raw, peeled potato from those plants as well as untransformed potatoes from the same parent line of potato have been safe and well tolerated in Phase I clinical trials for other expressed antigens.

HBsAg has been previously expressed in transgenic tobacco plants (a member of the solanaceae (potato) family). In that system, HBsAg was expressed at a level of 0.01% of the total soluble leaf protein. HBsAg particles that were equivalent to those derived from recombinant yeast derived HBsAg were found in extracts of the leaf tissues. When this material was administered intraperitoneally (i.p.) in combination with complete Freund's adjuvant (CFA) to mice, anti-HBS developed and there were no significant adverse events noted.

The lines of potatoes expressing HBsAg selected for use in accordance with these examples are transformed lines from *S. tuberosum L.* c.v. Frito-Lay 1607 HB-7. The transformed lines are designated FL-1607 HB-7 and HB114-16. To obtain these lines, the HBsAg gene from a pMT-SA clone of a Chinese a isolate of HBV was inserted into transformation plasmid vectors (pHB-7 and pHB114) that were mobilized into *Agrobacterium tumefaciens* (LBA4404) that was then used to transform *Solanum tuberosum* L cv. "Frito-Lay 1607." The plasmid vectors used to construct the potato lines pHB-7 and pHB114-16 used in these examples both contain the gene for neomycin phosphotransferase (NPTII, also known as APH(3')II). This gene also becomes integrated into the potato genome and is expressed in the potato cells. *E. coli* derived NPTII has been shown to be biochemically equivalent to plant expressed NPTII. The *E. coli* derived NPTII degrades rapidly under conditions of simulated mammalian digestion and has been shown to cause no deleterious effects when purified protein was fed to mice at up to 5 g/kg body weight. The transformed FL-1607 was cured of the *A. tumefaciens* and clonally propagated and the FL-1607 HB-7 and HB114-16 lines were selected for their high level of HBsAg expression. Extracts of the FL-1607 transformed lines were tested for HBsAg concentration by ELISA techniques. HB-7 averaged 1100 ng HBsAg per gram of tuber weight and HB114-16 averaged 8500 ng±2100 ng of HBsAg per gram of tuber weight.

In addition, the extracted HBsAg spontaneously forms virus like particles (VLPs) that sediment at the same density as yeast derived HBsAg VLPs. Electrophoretic mobility and western blot analysis indicates that the tuber expressed antigen is indistinguishable from yeast derived antigen.

The lines were clonally propagated to multiply the number of plants and potted in soil to produce the tubers used in the examples. The transformed lines were maintained by in vitro clonal propagation.

The untransformed parent potato line, FL-1607, was maintained by clonal propagation and potted to produce tubers that were used as the placebo control. The tissues from these tubers do not express any proteins that are reactive with reagents to detect HBsAg.

EXAMPLE 1

BALB/c mice were fed either peeled HB-7 potato slices or control non-transformed potatoes. Each group of mice was given three 5 gm feedings of potato on days 0, 7 and 14. The B subunit of cholera toxin (CT) (Sigma) was used as an oral adjuvant. Ten µg of the adjuvant was placed on the potato slices (both experimental and control) and consumed by the animals in conjunction with the antigen. The animals fed HB-7 therefore received an average of 5.5 µg HBsAg per feeding, or a total average does of 16.5 µg HBsAg over the 3 feedings provided.

Mice fed HB-7 developed serum IgM and IgG responses that were specific to HBsAg, whereas the group of animals fed control non-transformed potatoes failed to make any antibodies. After the third feeding an immune response was observed that peaked at around 70 mIU/ml. After a single i.p. inoculation of 0.5 µg of yeast derived recombinant HBsAg (rHBsAg) in alum (a normally subimmunogenic dose) a strong secondary response was observed that peaked at around 1700 mIU/ml. This response was predominantly IgG. No primary or secondary response was seen in the control mice fed non-transgenic potato and CT. Without the oral adjuvant, there was no significant response to HBsAg.

EXAMPLE 2

Further experiments have used the Frito-Lay 1607 HB114-16 line. In this line expression is driven from the 35S promoter and average tuber expression in the lot used for these experiments was 8.37 µg HBsAg/gm wet weight of tuber.

Groups of BALB/c mice (5/group) were fed either with HB114-16 or with control non-transgenic potato. In both cases 10 µg CT was added to the potato. The feeding was repeated one and two weeks later. The total average dose to each mouse of HBsAg in the transgenic potato was 125.55 μg over the 3-week period. Then, at the later of 70 days following the first feed or at 3-6 weeks after the initial immune response had returned to baseline levels, the mice were immunized with a sub-immunogenic (0.5 μg) dose of rHBsAg (Merck) delivered in aluminum adjuvant by subcutaneous (s.c.) injection.

At these dose levels an initial immune response was seen immediately after the second feeding. This immune response continued to rise and peaked at around 6 weeks at 100 mIU/ml. A titer of only 10 mIU/ml in a human after a three dose of a current licensed injectable hepatitis B vaccine is considered to reflect successful immunization. The response returned to baseline at 13 weeks and at 16 weeks the animals were given the boost dose of rHBsAg. This led to an immediate rise in immune titer to >3000 mIU/ml, which remained over 1000 mIU/ml for the remainder of the experiment (40 weeks). This established that the primary immunization generated antigen specific immune memory cells that were rapidly and strongly recalled upon secondary boosting.

The control animals for this experiment that were given non-transgenic potato+CT did not develop a significant immune response to HBsAg and upon secondary challenge with the subimmunogenic dose, as described above, no secondary response was seen establishing the specificity of the results. Controls given transgenic potato without CT only developed a low level, i.e. 10 mIU/ml titer for a primary response that that returned to baseline in only one week. Further challenge with the subimmunogenic dose as described above only gave a secondary response of 50 mIU/ml and return to only 10 mIU/ml in only two weeks.

EXAMPLE 3

The transgenic potato has also been used to boost a pre-existing sub-immunogenic dose of rHBsAg in mice. In this experiment groups of BALB/c mice (5/group) were immunized with a sub-immunogenic dose of rHBsAg (Merck) delivered s.c. in alum. 5 weeks later each mouse was fed either with HB114-16 or with control non-transgenic potato. In both cases 10 μg CT was added to the potato. The feeding was repeated one and two weeks later. The total average dose to each mouse was 125.55 μg over the 3-week period.

A secondary response developed that had started to appear at the time of the third feeding and which rose to approximately 1000 mIU/ml 11 weeks after the initial priming immunization before declining. In a control group no immune response developed in the group fed the non-transgenic potato.

EXAMPLE 4

Forty two human subjects testing free of HIV and being previously immunized with a commercial HB vaccine and after an extended time having anti-HBsAg titers below 115 mIU/ml, were fed potatoes containing HBsAg or an HBsAg free potato control in a randomized double blind study. When the code was broken, it was determined that Group 1 was a control group that received three doses of 100 grams of non-transgenic potato FL-1607. Group 2 received two doses of 100 grams each of transgenic potato FL-1607 HB114-16 and one dose of nontransgenic FL-1607 potato. Group 3 received three doses of 100 grams each of transgenic potato FL-1607 HB114-16.

Available pre-clinical data indicate that (1) on a weight basis, mice freely consume of up to 25% of their body weight in potato without evidence of toxicity and (2) a 50 μg dose of HBsAg in 5 gm of potato is immunogenic as a primary series with an oral adjuvant. The available clinical data with other potato vaccines indicate that (1) consumption of 100 gm of raw potato is generally well tolerated and (2) on a weight basis, 100 gm consumed by a 70 kg person would represent 0.14% of body weight. This amount is approximately 178-fold less than has been consumed, by weight, in mice in pre-clinical experiments.

Thus, in the example for humans, 100 to 110 gm of potato was ingested by volunteers per dose. The clinical lot scheduled for use in this study contained 8.5±2.1 μg of HBsAg per gm of potato. Subjects who received two 100 gm doses of transgenic potato received a total dose of 1,280 to 2,120 μg of HBsAg and subjects receiving three doses received a total of 1,920 to 3,180 μg of HBsAg over the course of 28 days.

On each day of dosing (days 0, 14 and 28) the appropriate number of potatoes for each group (placebo and control) were separately removed and processed into individual 100 to 110 gm doses by pharmacy personnel using clean techniques. Briefly, selected potatoes were washed, peeled, diced and placed into an ice-cold water bath. Peeling of the potatoes was done to remove the skin that contains the alkaloid solanine. This alkaloid can cause abdominal discomfort or nausea and may cause a bitter taste. Following peeling and dicing, 100 to 110 gm doses of potato was weighed out for each study subject according to group assignment and Subject Identification Number (SID). Peels and any unused portions of potatoes were collected and processed for destruction. Aliquots of potato for each study subject was kept under water to prevent browning from oxidation between the time the potato was diced until the study subject consumed it. An appropriate sample of processed potato from each group at each feeding was retained and frozen for further processing to verify antigen content.

The subjects were tested for anti-HBsAg titer on the days shown in Tables 1, 2, and 3. The results clearly show an increased response to the administered HBsAg antigen as a result of ingesting of the genetically transformed potatoes. Over 60 percent of the subjects receiving three doses of potatoes containing HBsAg showed a significant increase in immune response. The tables clearly indicate that, in many cases, ingesting of plant material containing genetically expressed HBsAg can act as an effective booster for primary HB vaccination. None of the control subjects that received three doses of non-transgenic control potatoes had any change in antibody titer over the entire course of the observation.

What is claimed is:

1. A method for providing a serum IgM and IgG response specific to hepatitis B surface antigen (HBsAg), in an animal by feeding the animal with a substance comprising a physiologically acceptable plant material containing hepatitis B surface antigen in combination with an adjuvant, said com-

TABLE 1

Group 1 (Received 3 doses of Nontransgenic potato tuber) Titer (lm/ml)

| Volunteers | Day 0 | Day 7 | Day 14 | Day 21 | Day 28 | Day 35 | Day 42 | Day 56 |
|---|---|---|---|---|---|---|---|---|
| 1 | 72 | 64 | 73 | 74 | 78 | 78 | 63 | 57 |
| 2 | 17 | 14 | 12 | 12 | 2 | 5 | 10 | * |
| 3 | 63 | 51 | 56 | 67 | 69 | 74 | 88 | 89 |
| 4 | 66 | 78 | 52 | 62 | 54 | 74 | 67 | 69 |
| 5 | 0 | 0 | 0 | 1 | 0 | 0 | * | 7 |
| 6 | 12 | 9 | 12 | 18 | 18 | 16 | 17 | 19 |
| 7 | 34 | 28 | 24 | 32 | 33 | 29 | 34 | 33 |
| 8 | 9 | 11 | 12 | 11 | 8 | 7 | 9 | 9 |
| 9 | 104 | 99 | 83 | 110 | 120 | 100 | 99 | 92 |

* No Sample Drawn

TABLE 2

Group 2 (Received 2 doses of Transgenic & 1 dose of Nontransgenic potato tuber) Titer (mIU/ml)

| Volunteers | Day 0 | Day 7 | Day 14 | Day 21 | Day 28 | Day 35 | Day 42 | Day 56 |
|---|---|---|---|---|---|---|---|---|
| 1 | 29 | 29 | 29 | 29 | 29 | 29 | 47 | 93 |
| 2 | 8 | 15 | 27 | 49 | 41 | 40 | 73 | 79 |
| 3 | 170 | 161 | 158 | 144 | 130 | 144 | * | 132 |
| 4 | 32 | 32 | 31 | 34 | 33 | 23 | * | 42 |
| 5 | 13 | 15 | 15 | 14 | 11 | 11 | 17 | 17 |
| 6 | 43 | 37 | 46 | 77 | 69 | 85 | 85 | 78 |
| 7 | 67 | 37 | 47 | 57 | 80 | 89 | 77 | 73 |
| 8 | 11 | 7 | 114 | 114 | 136 | 176 | 191 | 200 |
| 9 | 104 | 126 | 262 | 269 | 318 | 313 | 357 | 390 |
| 10 | 33 | 26 | 22 | 21 | 21 | 25 | 25 | 29 |
| 11 | 107 | 92 | 96 | 89 | 93 | 83 | 95 | 90 |
| 12 | 21 | 22 | 55 | 112 | 120 | 219 | 395 | 458 |
| 13 | 65 | 68 | 66 | 63 | 89 | 103 | 137 | 258 |
| 14 | 20 | 24 | 18 | 15 | 12 | 12 | 15 | 20 |
| 15 | 0 | 0 | 0 | 0 | 0 | 0 | 0 | 0 |
| 16 | 97 | 93 | 112 | 109 | 128 | 294 | 454 | 432 |
| 17 | 26 | 34 | 197 | 330 | 353 | 360 | 707 | 863 |

* No Sample Drawn

TABLE 3

Group 3 (Received 3 doses of Transgenic potato tuber) Titer (mIU/ml)

| Volunteers | Day 0 | Day 7 | Day 14 | Day 21 | Day 28 | Day 35 | Day 42 | Day 56 |
|---|---|---|---|---|---|---|---|---|
| 1 | 17 | 20 | 70 | 140 | 269 | 428 | 401 | 463 |
| 2 | 94 | 87 | 100 | 99 | 88 | 79 | 87 | 88 |
| 3 | 33 | 34 | 32 | 33 | 27 | 34 | 31 | 32 |
| 4 | 0 | 0 | 0 | 0 | 0 | 0 | 0 | 0 |
| 5 | 9 | 9 | 53 | 74 | 74 | 85 | 65 | 61 |
| 6 | 20 | 41 | 57 | 84 | 452 | 475 | 897 | 652 |
| 7 | 85 | 76 | 496 | 1212 | 3058 | 3572 | 4152 | 4526 |
| 8 | 13 | 19 | 19 | 15 | 28 | 14 | 20 | 21 |
| 9 | 120 | 236 | 282 | 390 | 605 | 667 | 1583 | 1717 |
| 10 | 9 | 11 | 14 | 13 | 13 | 18 | 11 | 15 |
| 11 | 0 | 0 | 0 | 0 | 0 | 0 | 0 | 0 |
| 12 | 72 | 77 | 137 | 270 | 349 | 523 | 1098 | 1226 |
| 13 | 85 | 76 | 84 | 74 | 111 | 215 | 175 | 163 |
| 14 | 40 | 35 | 39 | 71 | 119 | 122 | 330 | 430 |
| 15 | 56 | 51 | 59 | 85 | 252 | 407 | 520 | 745 |
| 16 | 115 | 213 | 511 | 1054 | 1964 | 3069 | 2966 | 3449 | bination causing serum IgM and IgG responses specific to HBsAg in excess of serum IgM and IgG responses specific to HBsAg caused by HBsAg alone.

2. The method of claim 1 wherein the animal is a human.

3. The method of claim 2 wherein the plant material is from a plant that has been genetically altered to express said antigen.

4. The method of claim 3 wherein the human ingests sufficient plant material to provide from about 10 to about 100 micrograms of hepatitis B surface antigen per kilogram of body weight of the human.

5. The method of claim 4 wherein the human ingests sufficient plant material to provide from about 2 to about 5 grams of plant material per kilogram of body weight of the human.

6. The method of claim 3 wherein the human ingests said plant material a plurality of different times, said times being separated from each other by at least 5 days.

7. The method of claim 4 wherein the human ingests said plant material a plurality of different times, said times being separated from each other by at least 5 days.

8. The method of claim 5 wherein the human ingests said plant material a plurality of different times, said times being separated from each other by at least 5 days.

9. The method of claim 6 wherein the plurality of times is three times.

10. The method of claim 7 wherein the plurality of times is three times.

11. The method of claim 8 wherein the plurality of times is three times.

12. The method of claim 3 wherein the plant material is a material from a plant of the family Solanaceae.

13. The method of claim 4 wherein the plant material is a material from a plant of the family Solanaceae.

14. The method of claim 12 wherein the plant is a potato.

15. The method of claim 13 wherein the plant is a potato.

16. The method of claim 12 wherein the plant is a tomato.

\* \* \* \* \*

UNITED STATES PATENT AND TRADEMARK OFFICE
CERTIFICATE OF CORRECTION

| | | |
|---|---|---|
| PATENT NO. | : 7,527,810 B1 | |
| APPLICATION NO. | : 09/420695 | |
| DATED | : May 5, 2009 | |
| INVENTOR(S) | : Yasmin Thanvala et al. | |

It is certified that error appears in the above-identified patent and that said Letters Patent is hereby corrected as shown below:

In the STATEMENT REGARDING FEDERALLY SPONSORED RESEARCH,
Column 1, line 14,
please delete, "This invention was made with funding from the National Institute of Health award AI 42836, AI 27976. The United States Government may have certain rights in this invention."

and please insert,

--This invention was made with government support under AI042836 and AI027976 awarded by National Institutes of Health. The government has certain rights in the invention.--

Signed and Sealed this
Twelfth Day of June, 2012

David J. Kappos
*Director of the United States Patent and Trademark Office*